US009241808B2

(12) United States Patent
Sabatino (10) Patent No.: US 9,241,808 B2
(45) Date of Patent: Jan. 26, 2016

(54) AUXETIC PROSTHETIC IMPLANT

(71) Applicant: Anthony Sabatino, Carmel, IN (US)

(72) Inventor: Anthony Sabatino, Carmel, IN (US)

( * ) Notice: Subject to any disclaimer, the term of this patent is extended or adjusted under 35 U.S.C. 154(b) by 155 days.

(21) Appl. No.: 13/974,441

(22) Filed: Aug. 23, 2013

(65) Prior Publication Data

US 2014/0058517 A1    Feb. 27, 2014

Related U.S. Application Data

(60) Provisional application No. 61/693,608, filed on Aug. 27, 2012.

(51) Int. Cl.
*A61F 2/44* (2006.01)
*A61F 2/30* (2006.01)

(52) U.S. Cl.
CPC ..... *A61F 2/4425* (2013.01); *A61F 2002/30462* (2013.01)

(58) Field of Classification Search
CPC .................. A61F 2/4425; A61F 2002/30462
USPC ......... 606/246, 279; 623/17.11, 17.14, 17.15, 623/17.16
See application file for complete search history.

(56) References Cited

U.S. PATENT DOCUMENTS

| 5,108,413 | A | 4/1992 | Moyers |
| 6,376,573 | B1 * | 4/2002 | White et al. ................. 523/115 |
| 8,002,879 | B2 | 8/2011 | Hook |
| 8,034,103 | B2 | 10/2011 | Burriesci et al. |
| 2003/0233146 | A1 * | 12/2003 | Grinberg et al. ........... 623/17.14 |
| 2005/0003011 | A1 | 1/2005 | Sridharan et al. |
| 2006/0129227 | A1 | 6/2006 | Hengelmolen |
| 2007/0213838 | A1 | 9/2007 | Hengelmolen |
| 2008/0125771 | A1 | 5/2008 | Lau et al. |
| 2009/0239049 | A1 | 9/2009 | Hook et al. |
| 2010/0305535 | A1 | 12/2010 | Leeming et al. |
| 2011/0029063 | A1 | 2/2011 | Ma et al. |
| 2011/0046715 | A1 | 2/2011 | Ugbolue et al. |
| 2011/0282452 | A1 * | 11/2011 | Koerner et al. ............ 623/16.11 |

FOREIGN PATENT DOCUMENTS

| EP | 1239899 B1 | 6/2004 |
| WO | 2006131716 A2 | 12/2006 |

* cited by examiner

*Primary Examiner* — Pedro Philogene
*Assistant Examiner* — David C Comstock
(74) *Attorney, Agent, or Firm* — Krieg DeVault LLP (57) ABSTRACT

An implant including a first disc portion shaped and sized generally to correspond to a first intervertebral disc section having a pivot point positioned relative to a first surface opposite a second surface of the first disc portion and a lattice structure with a negative Poisson's ratio; a second disc portion being shaped and sized generally to correspond to a second intervertebral disc section having a pivot point receptacle positioned relative to a third surface opposite a forth surface of the second disc portion and a lattice structure with a negative Poisson's ratio where the first disc portion and the second disc portion are configured to exhibit an auxetic behavior when subject to compression generally perpendicular to a surface plane of the first surface and the second surface.

21 Claims, 4 Drawing Sheets

AUXETIC PROSTHETIC IMPLANT

TECHNICAL FIELD

The present invention relates to the field of implants, and more particularly, but not exclusively, to artificial disc implants.

Low back pain affects about 80% of all people sometime during their lives. Much of the chronic pain that patients experience can be attributed to the intervertebral discs, which can account for up to forty percent of those with chronic spine pain. Intervertebral discs are subjected to major stresses throughout a person's lifetime. Disc desiccation and internal disc disruption cause debilitating pain and reliance on the healthcare system including hospital admissions and disability. Current methods for treatment of chronic back pain include medications, physiotherapy, interventional spinal procedures and surgical remedies including spinal fusion and stabilization procedures. The two most common spinal procedures, discectomy and fusion, are not ideal for treating degenerative disc disease. Although discectomy has a reasonably good short-term effect in relieving radicular pain, it can cause disc space height reduction that can further increase the instability of the treated disc. Current methods of spinal fusion can include complications such as infection, hardware incompatibility and postoperative pain.

Current state of the art disc replacement surgeries employ titanium implants with polyethylene core inserts. Several types include composite discs (Charite, Bryan, Prodisc), hydraulic discs, elastic discs (Acroflex), and mechanical discs (Maverick, FlexiCore). Problems inherent to these designs include mismatch between the metal plates and the vertebral body bone shape, polyethylene issues of long term wear and tear with potential revision, inadequate anchoring issues, lack of coating, and excessive concentrated forces due to metal on metal interfaces.

A "one size fits all" approach in patients undergoing disc replacement with titanium implants fails to meet the demands necessary for long term success, i.e. the viability of the disc endplate interface and the avoidance of infection and reoperation. Lack of flexibility, inherent to most alloys used in current disc replacement technology, creates excessive forces at sub and supra-adjacent spinal segments. Concomitant stresses to the facet joints can be related to distraction of the endplates and stress on the joints secondary to high stiffness of the alloy. Over distraction or separation in a functional spinal unit which includes two adjacent vertebrae, an intervertebral disc and the adjoining ligaments can cause fractures to the facet joint and pars interarticulars as well as leg and back pain.

Other complications include, osteolysis, whereby the body begins to absorb living bone tissue around the disc replacement causing pain. Severe complications can require subsequent medical procedures. Other possible complications include loss of motion and weakening of the spinal column. For a patient who has undergone an anterior approach with initial disc replacement surgery, reoperation can cause complications. Complications due to additional surgical exposure can include scar tissue formation and bleeding from exposure of the vessels anterior to the spinal column.

An implant device should be able to maintain disc height while allowing full range of motion for the spinal segment. Correct sizing of the implant contributes to long term stability and likely mitigates the need for subsequent medical procedures. For shock absorbing quality and the ability to handle shear stresses applied to the spinal segment, the implant should have a structure that is strong, lightweight and can withstand the forces applied in multiple directions. Durability and biocompatibility correlate to long-term success.

The need for more effective solutions and treatments for low back pain is great from an economic and medical point of view. Due to the technical structure and function of an intervertebral disc, the evolution of the perfect disc prosthesis has been slow in coming. Present approaches to artificial disc implants suffer from a variety of drawbacks, limitations, disadvantages and problems including those respecting maintaining structure and full range of motion as well as others. There is a need for the unique and inventive artificial disc implant apparatuses, systems and methods disclosed herein.

SUMMARY

One embodiment of the present invention comprises a novel artificial disc implant. Other embodiments include apparatuses, systems, devices, hardware, methods, and combinations for artificial disc implants. Further embodiments, forms, features, aspects, benefits, and advantages of the present application shall become apparent from the description and figures provided herewith.

Figure 1:
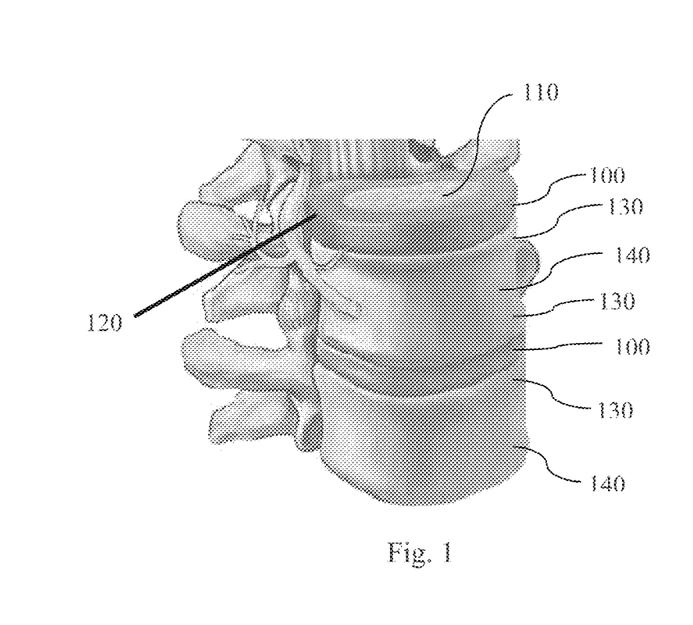
FIG. 1 is an illustration of a functional spinal unit.
Figure 1A:
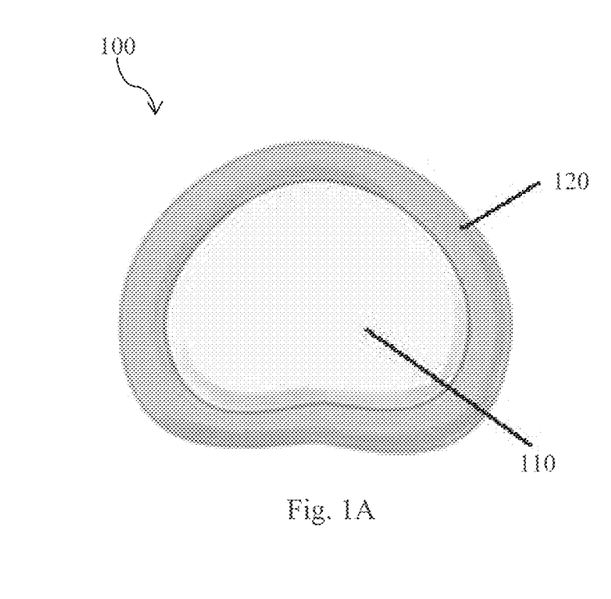
FIG. 1A is an illustration of an intervertebral disc of the functional spinal unit of FIG. 1.

Intervertebral disc degeneration can occur in patients at an age younger than hip or knee degeneration. In a healthy disc as shown in FIGS. 1 and 1A, the outer annulus 120 is able to withstand high tensile stress and elastic deformation. Torsion forces are well tolerated in multiple directions. The nucleus 110, which is enclosed within the annulus 120 and endplates 130 of the vertebrae 140, is composed of glycosaminoglycan. The matrix within the nucleus 110 interfaces with the cartilaginous endplate 130 of the vertebrae 140 to act as a shock absorber and a facilitator of nutrient delivery between the disc 100 and endplate 130. A breach in the integrity of the composition within the annulus 120/nucleus 110 structure could lead to compromised function, pain and long-term disability.

Functionally, the intervertebral disc performs two important, but somewhat conflicting, duties: it maintains spinal column stability while providing the anterior column with necessary flexibility. Surgical procedures involving the spine can compromise the stability and flexibility of the intervertebral disc leading to advanced degeneration.

An artificial disc employing the characteristics and properties of auxetic materials is proposed for applications with axial loading of the spine. Further features including 3D-CAD specific modeling, additive layer manufacturing and nano-porous surface coatings with an Arginine-Glycine-Aspartic (RGD) acid peptide can provide enhanced long term efficacy, decreased incidence of infectious complications, long term durability, patient acceptance and stem cell enhanced vascular viability.

The design described herein provides an intervertebral prosthetic disc with several features including patient specificity, low weight, high tensile strength in relation to weight, an auxetic composition, antimicrobial properties and an ability to maintain viability at the disc endplate interface due in part to stem cell vessel penetration.

DETAILED DESCRIPTION OF ILLUSTRATIVE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
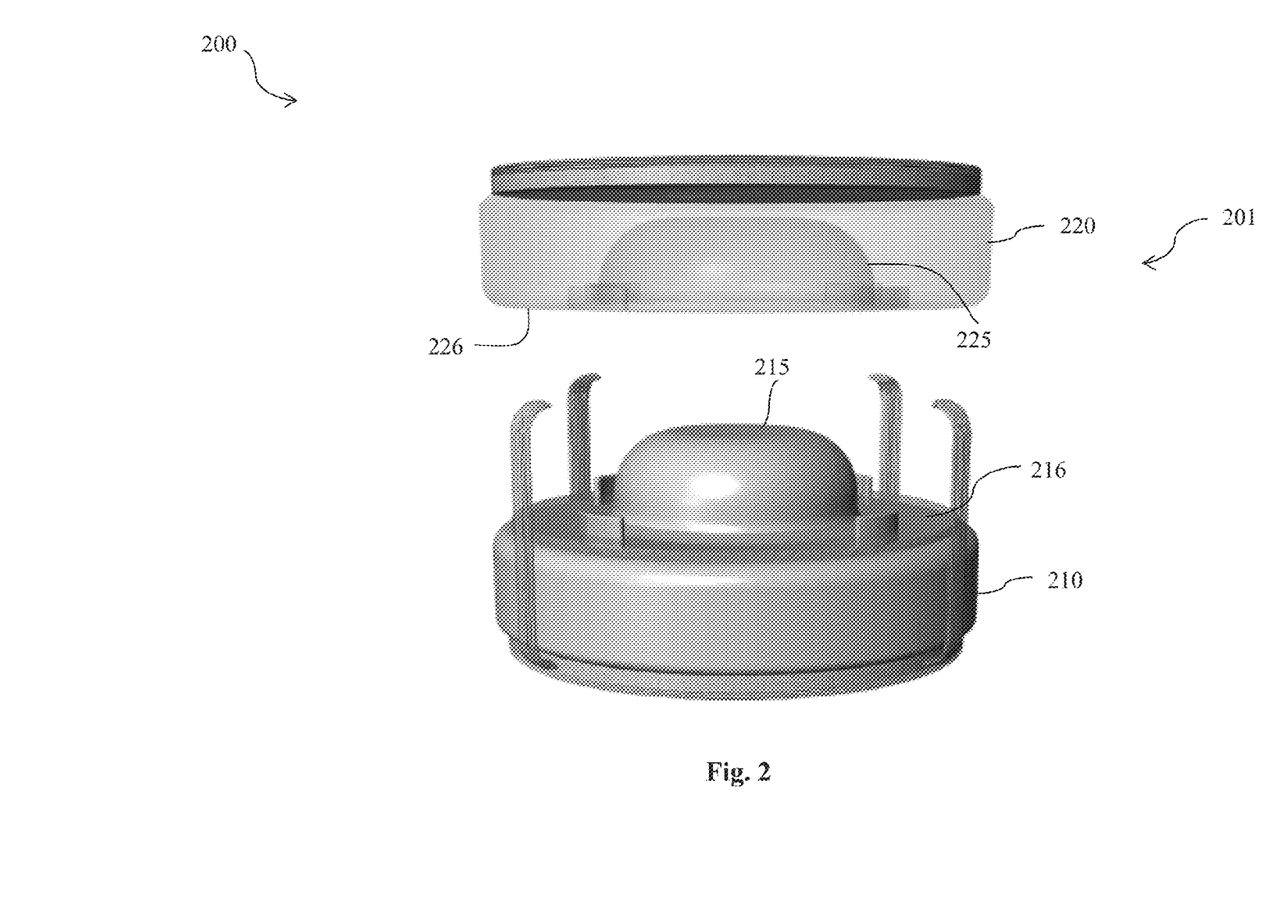
FIG. 2 is partially transparent view of an illustration of an embodiment of the present application.

With reference to FIG. 2, a two-piece intervertebral implant device 200 is shown to have two disc portions 210, 220. The two disc portions 210,220 are shaped and sized generally to correspond to two sections of an intervertebral disc 201. The two piece design of the implant provides a mode of flexibility in the implant. The first disc portion 210 includes a pivot point 215 positioned on a surface 216 of the first disc portion 210. The second disc portion 220 includes a pivot point receptacle 225 on a mating surface 226 of the second disc portion 220. The range of motion between the pivot point 215 of the first disc portion 210 and the pivot point receptacle 225 of the second disc portion 220 provides a degree of freedom which corresponds to a degree of flexibility.

Each disc portion 210,220 has a lattice structure with a negative Poisson's ratio. The Poisson's ratio of a material is expressed as the ratio of lateral strain to the longitudinal strain for a material undergoing tension in the longitudinal direction. A negative Poisson's ratio occurs due to changes in the structure and geometrical makeup of the substance, allowing it to react differently to strain, stress and uniaxial loading. On a micro-molecular and macro-molecular basis, auxetic substances demonstrate very high tensile strengths. Because of high-tensile strength and lightweight properties, auxetic materials are suitable for a wide range of medical applications.

Auxetic substances can include alloys, composites, fibers or foams. Auxetic materials have a negative Poisson's ratio. When stretched, these materials expand in the plane approximately perpendicular to the applied force. When compressed, auxetic material contracts in a plane approximately perpendicular to the applied force. Perpendicular is not an exact mathematical term but considered relative and in a general sense being orthogonal to one another. Further, the degree of the expansion or contraction reaction can vary among various perpendicular planes.

Figure 3:
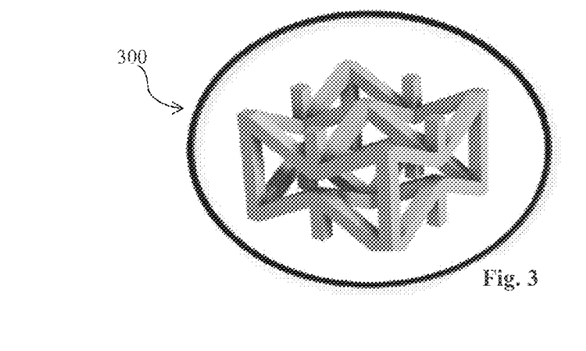
FIG. 3 is an illustration of an auxetic lattice structure.

FIG. 3 shows one form of lattice structure 300 of the first disc portion 210 and the second disc portion 220. The lattice structure 300 provides auxetic behavior when subject to compression perpendicular to a surface plane parallel to at least one of the surface 216 of the first disc portion 210 and the mating surface 226 of the second disc portion 220.

In one embodiment, an auxetic material can be formed by a material having a lattice structure that exhibits a negative Poisson's ratio when subjected to compressive and tensile forces. Auxetic lattice structures provide this counter-intuitive behavior due to intricate spatial microstructures. The structures can include but are not limited to inverted cell structures, re-entrant cell structures, concave cells, and hexagonal chiral lattice structures, to name a few. One specific auxetic material is a highly anisotropic expanded porous polytetrafluoroethylene.

The ability to dilate when stretched and contract when compressed occurs due to hinge-like structures which flex when subjected to forces. Structures exhibiting auxetic configurations have properties including a high shear modulus, high resistance to indentation, high fracture toughness and the ability to withstand compressive loads. Auxetic material can provide fracture resistance with high energy absorption to maintain the integrity of the device. A high shear modulus allows the device to withstand shear stresses applied in multiple directions. Stability can be aided with high shear modulus and fracture toughness. High hardness and the ability to withstand compression provide durability to maintain shape, shock absorption, and flexibility. These properties contribute to an auxetic implant's ability to mimic the properties of an intervertebral disc.

Negative Poisson ratios in the −0.3 range can maximize the beneficial effects of this auxetic substances. In a substance with a positive Poisson's ratio, compression of an intervertebral disc could lead to encroachment on the surrounding spinal structures due to the expansion of the disc. In an auxetic intervertebral disc exhibiting a negative Poisson's ratio, the decrease in transverse expansion with compression of an artificial disc could prevent the impingement of nerves and surrounding neural structures while still maintaining range of motion and limiting stress.

Spinal dynamics place stress forces at the level of the implant as well as supra and subjacent levels inherent to postoperative disc replacements. Auxetic alloys demonstrating a negative Poisson's ratio have advantages over non-auxetic prosthetics because of improved biomechanical dynamics leading to less concentrated stress on the implant which could lead to increased longevity of the implant and a decreased incidence of reoperation.

Auxetic lattice design alloys with a negative Poisson's ratio can have improved fracture toughness, shear modulus, and high fatigue strength, as well as increased fracture, creep and impact resistance. An auxetic alloy design allows for lightweight implants with high tensile strengths on a per weight basis. Compression stiffness at low weights would still be in the range of 850 N/mm-2,500N/mm (In Vivo disc approx. 1,560N/mm). One embodiment of an anisotropic alloy with a negative Poisson's ratio could prevent encroachment of surrounding spinal structures upon compression in the longitudinal spinal axis. Alloys having isotropic properties can also be considered.

An auxetic based composite/alloy intervertebral disc implant demonstrating a negative Poisson's ratio could allow for maintaining spinal motion, decreasing stress on supra and infra-adjacent spinal segments and, because of the inherent properties of auxetic materials, limiting the expansion and therefore the infringement upon surrounding nerves, ligaments and spinal neural canals. Spinal motion in multiple planes could be preserved. Features of various embodiments can include carbon based nanotubes with auxetic properties including but not limited to carbon graphite vaporized by laser, memory-shaped alloys with lattice design, manufacturing of powder-based substance using selective electron beam melting principles and/or via additive layer manufacturing. Properties can include pseudo-elasticity and shape memory effect. Composite alloys of Nickel-Titanium, CuZnAl and CuAlNi in the austenite phase could be considered.

Figure 4:
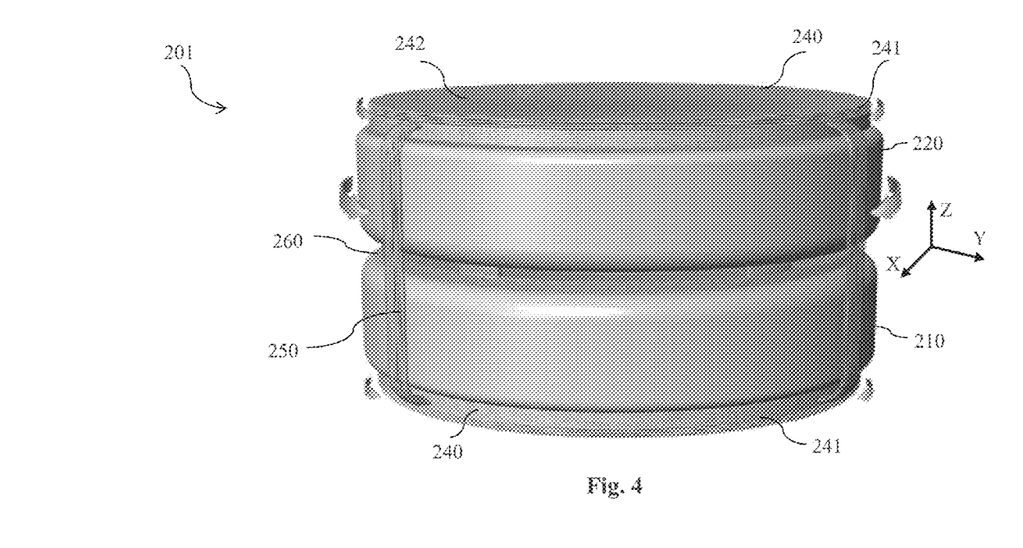
FIG. 4 is an illustration of a device of one embodiment of the present application.
Figure 5:
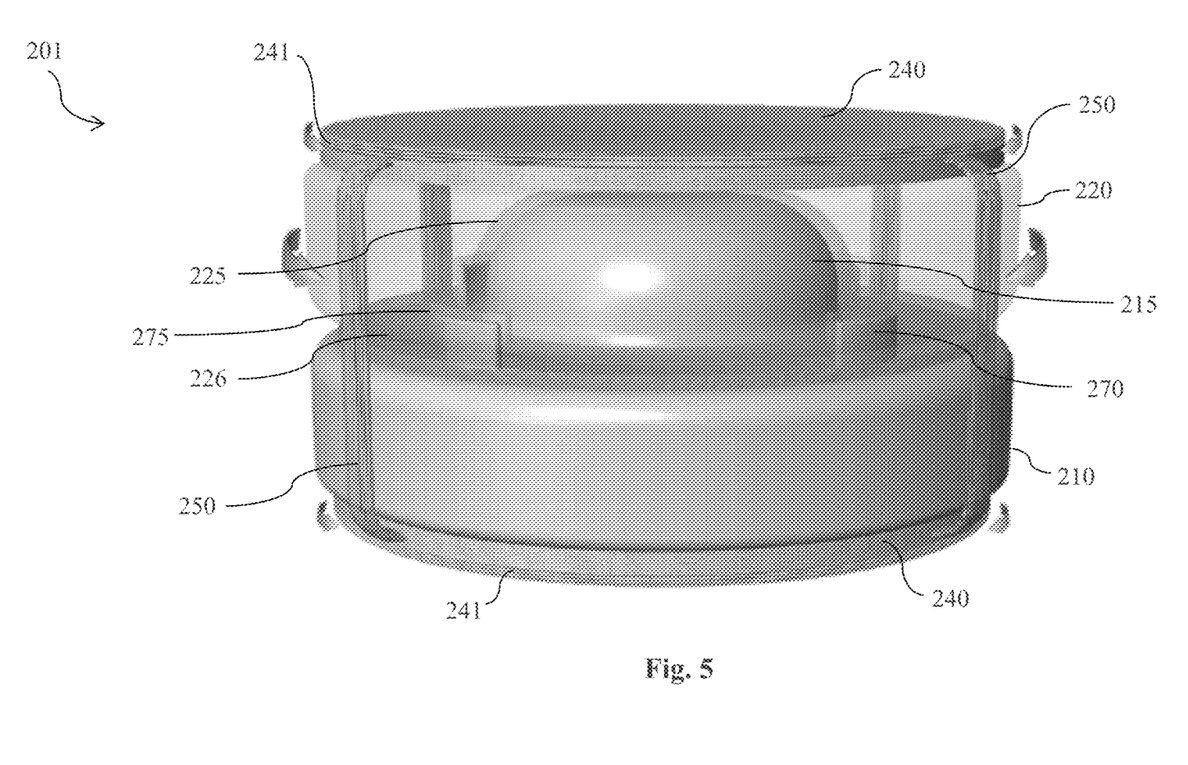
FIG. 5 is a partially transparent view of an illustration of two portions of the embodiment of FIG. 4.

With reference to FIG. 4 and FIG. 5, a two piece construction of a one-piece fit design of an intervertebral disc 201 includes male 210 and female 220 disc portions which fit together having a set of extensions 250. The male disc portion 210 includes an auxetic lattice structure (see FIG. 3) with a pivot point 215 in a center region and a locating feature 270 to limit torsion beyond a specified range.

Male disc portion 210 is shown in FIG. 5 with multiple locating bosses or pegs within slots or pockets 275 on the female disc portion 220. Adequate tolerance can be provided to allow limited movement between the locating features 270,275. The dimensions and design of the locating feature of the male portion 210 and locating pocket of the female portion 220 can vary and be determined by one skilled in the art. In another further embodiment, an interlocking design of the male portion 210 and the female portion 220 could both facilitate rotation, flexion, extension and side bending and limit rotation through interlocking pins or plates thereby limiting torsion and stress on the posterior facet joints.

Complement to the male disc portion 210, the female disc portion 220 includes a similar auxetic lattice structure (see FIG. 3) which accepts the pivot point 215 of the male disc portion 210 and the locating feature 270 allowing torsional rotation. In one embodiment, concavity 225 of the mating surface 226 of the female disc portion 220 is hemispheric allowing the pivot point 215 from the male disc portion 210 to rotate in multiple axes (flexion, extension, left and right lateral bending, left and right axial rotation) of a conventional coordinate system with X,Y, Z as known in the art. Concavity 225 can vary to include elliptical or irregular shapes and can have varying curvatures applied in different location on the concavity.

Various numbers of channels or extensions 250 shown in FIG. 4 and FIG. 5 can be added to facilitate the one-piece fit design of the intervertebral disc 201. In various embodiments, the extensions 250 can provide for the migration of stem cells or other biological material. The addition of these channels 250 can depend on the channel material's ability to accept the diffusion of stem cell via an auxetic lattice structure. The extensions 250 can be structured in various embodiments to flex under pressure, to be compressed under pressure and can have or cannot have a hard connection with the endplate.

In one embodiment, the male disc portion 210 can include an elastomer coating 260. The coating can include a type 1 collagen, fibronetin or RGD peptide. Nano-porous surfaces can be created using these substances which can exhibit special antimicrobial characteristics and could allow stem cell transmission and growth across the bone implant barrier, thereby mitigating infection and further degeneration. In a further embodiment, an internal cushion design for the male and female disc portions 210,220 can include a smart material for shock absorption in the outer covering at the male/female interface.

FIG. 4 and FIG. 5 also show endplates 240 at the interface between the implant disc 200 and a vertebral endplate (not shown). In various embodiments, endplates 240 can have a nano-porous surface 242 made up of fibronectin/RGD protein coating which allows stem cell penetration and insures antimicrobial activity, adherence and endplate viability. The nano-porous material of the endplate surface 242 can be structured to allow biological material such as stem cells to transfer between the implant and the surrounding tissue. In other embodiments, the endplates 240 can include outer threads 241 to allow seating of the device within the cancellous bone of the vertebral body. Though the endplates 240 shown in the figures have a relatively planar surface, the surface geometry or contour can vary depending on the application of the implant and the anatomy of a patient. In one specific embodiment, the contour of the endplate follows the contour of the mating vertebral endplate.

Various anchoring mechanisms to the vertebral endplates as known in the art can be considered including an anchor screw, side supports and male/female components and the like. In one embodiment, the endplates 240 can include outer threads 241 which allow fixation without the need for screws or posterior hardware. In a further embodiment, a microporous coating on the endplates 240 and the outer threads 241 can promote ingrowth at the bone/implant juncture.

For embodiments with a nano-porous or metalloporous surface, the implant-vertebral endplate interface 242 can allow stem cell propagation, vessel formation and nutrient exchange. Without an exchange of nutrients and an uninterrupted supply of blood flow, the bone tissue can die and the bone collapse. The endplate 240 could allow for increased viability at the level of the spongiosum layer of the vertebral endplate, leading to decreased bone re-sorption and less chance for osteonecrosis.

Infection is possible in any operative procedure in which prosthetic implants are employed. Employing an implant with a nano-porous surface can reduce the incidence of infection due to the antimicrobial surface characteristics of the implant. The surface of the implant-vertebral interface due to its elemental properties could have antimicrobial characteristics mitigating the incidence of infection and could lead to increased biocompatibility. In various embodiments, substrates suitable for these purposes demonstrating biocompatibility can include fibronectin coated surfaces as well as RGD conjugated silicone elastomers such as poly(dimethylsiloxane) (PDMS) developed through photochemical immobilization.

For one embodiment, an implant manufactured with a trabecular composition structure having micro-porous channels could facilitate vessel rich stem cells to traverse the trabecular composition structure leading to enhanced viability at the prosthetic/bone interface. The trabecular structure can include a higher surface area and is highly vascular with tiny lattice shaped spicules. The traversal of vessel rich stem cells through the trabecular structure could lead to a decreased incidence of osteolysis and an increased maintenance of nutrient delivery at the endplate/osseous junction. Long-term viability could be enhanced and further breakdown could be minimized.

One embodiment of the present application can include a micro-porous/metallic interface coated with either type 1 collagen, fibronectin, or the RGD peptide and positioned between a memory-shape alloy with a lattice structure exhibiting auxetic properties and the vertebral endplate to maintain the biological interface. This embodiment could preserve the nutrient transfer associated with non-desiccated discs at the endplate. Stem cells in the range of 10-20 microns could be capable of traversing the implant from one endplate through the extensions to the other endplate, thereby delivering nutrients across the disc space, actually improving the blood supply normally deficient in the human intervertebral disc.

Increased pain due to size incompatibility of the implant and unrestricted motion due to loss of surrounding supporting structures following implantation can lead to chronic pain, disability and lack of patient satisfaction. Using 3D-CAD modeling for sizing an implant to the individual patient could successfully mitigate mismatch of the implant leading to less postoperative back and leg pain. Furthermore, an implant with limited torsion in the horizontal plane would lead to less stress on the implant and the three-joint complex, including the posterior elements of the spine, including the facets. An implant with these properties could provide less postoperative stress fractures, less postoperative pain, and decreased incidents of reoperation.

Sizing requirements for disc prosthetics have historically been left to chance and a random one size fits all approach. Unfortunately, poor dynamics after implant can lead to failure, incompatibility and excessive forces on surrounding structures including nerves, ligaments, and facet joints. Such an incompatibility can lead to pain, disability and further surgery, including removal of the implant.

Further embodiments can include 3D-CAD modeling of a patient's intervertebral disc via computerized axial tomography based coordinates. In other embodiments, the modeling can be based on MRI data. An auxetic prosthetic intervertebral disc with a negative Poisson's ratio using a 3D-CAD design is described, creating a substantially near replica of a diseased disc, and reducing compatibility issues by employing rapid manufacturing with additive layer manufacturing (ALM) techniques. Coordinates obtained from MRI or Computerized Axial Tomography can serve as the instrument to construct the coordinates for 3D modeling.

The 3D-CAD model can be used to produce the two disc portions through ALM. The ALM of the two disc portions includes forming a lattice structure configured to exhibit an auxetic behavior when subject to compression along the longitudinal axis of the spine. The additive layers of the ALM process are assembled and joined to provide a sequential configuration of layers of the two disc portions. Creating a 3D-CAD prosthesis based on Cartesian coordinates could allow a true fit at the spinal segment destined for replacement.

Manufacturing techniques can aid in the application of implants having auxetic materials and nano-porous surfaces. The field of 3D-CAD modeling and 3-D printing can allow production of biocompatible substances/devices that could exceed the compressive strengths of bone, be lightweight, facilitate compression without encroachment on surrounding structures, and could be unique to the individual requiring the device or implant. In one embodiment, the 3-D printing can include using ALM by laser sintering beam technology.

Surgical methods for disc arthroplasty vary. Embodiments of this application allow for an anterior or lateral approach using sound and well documented techniques. Although the composition of the lattice structure can have variability, an auxetic composition with negative Poisson's ratio is described.

One aspect of the present application is a device including a first disc portion shaped and sized to correspond generally to a first intervertebral disc section having a pivot point positioned on a first surface opposite a second surface of the first disc portion and a first lattice structure with a negative Poisson's ratio and a second disc portion shaped and sized to correspond generally to a second intervertebral disc section having a pivot point receptacle positioned on a third surface opposite a fourth surface of the second disc portion; a second lattice structure with a negative Poisson's ratio. The first disc portion is positioned relative to the second disc portion with the pivot point of the first disc portion within the pivot point receptacle of the second disc portion and the first surface of the first disc portion adjacent to the third surface of the second disc portion. The first disc portion and the second disc portion are configured to exhibit an auxetic behavior when subject to compression approximately perpendicular to a surface plane parallel to at least one of the first surface, the second surface, the third surface and the fourth surface.

Features of this aspect can include the first disc portion having an endplate positioned adjacent the second surface on the first disc portion, the endplate can include a threaded portion, and the endplate including a nano-porous material structured to allow biological material transfer. Still further features can include the second disc portion having a second endplate approximate the fourth surface on the second disc portion, at least one vertical extension extending along a first outer surface of the first disc portion and a second outer surface of the second disc portion from a position approximate the second surface to a position approximate the fourth surface, the extension being orthogonal to the surface plane which is parallel to at least one of the first surface, the second surface, the third surface and the fourth surface.

Further features of this aspect of the present application can include the at least one vertical extension having micro-porous channels with trabecular characteristics, the first disc portion having an additive layer disc portion, the additive layer disc portion having a plurality of layers joined to provide a sequential configuration of the first intervertebral disc section, and the second disc portion having a second additive layer disc portion with a plurality of layers joined to provide a sequential configuration of the second intervertebral disc section.

Another aspect of the present application is a device including a first disc portion of an intervertebral disc having a pivot point positioned relative to a first surface of the first disc portion; and a second disc portion of the intervertebral disc having a pivot point receptacle positioned relative to a second surface of the second disc portion. The pivot point on the first surface of the first disc portion is positioned with respect to the pivot point receptacle on the second surface of the second disc portion to form the intervertebral disc. The first disc portion and the second disc portion each have a lattice structure configured to exhibit a negative Poisson's ratio when subject to compression perpendicular to a plane parallel to at least one of the first surface and the second surface.

Features of this aspect can include the first disc portion having an endplate positioned opposite the first surface on the first disc portion, the endplate having at least one feature selected from a group comprising antimicrobial characteristics, a nano-porous structure, outer threads, and a trabecular structure to allow biological material transfer, and the second disc portion having the endplate. A further feature of this aspect can include the first disc portion having at least one vertical extension having micro-porous channels with trabecular characteristics, the first disc portion having an additive layer disc structure and the second disc portion having a second additive layer disc structure, and the additive layer disc structure having a plurality of layers joined to provide a sequential configuration of the first disc portion of the intervertebral disc and the second additive layer disc structure having a plurality of layers joined to provide a sequential configuration of the second disc portion of the intervertebral disc.

Yet another aspect of the present application is a method including analyzing an intervertebral space with a patient's intervertebral disc; creating a disc model in response to said analyzing; forming a first disc portion and a second disc portion with a plurality of additive layers in response to the disc model, each having a lattice structure configured to exhibit an auxetic behavior; and replacing the patient's intervertebral disc with an implant disc including the first disc portion and the second disc portion. Features of this aspect can include joining a set of additive layers of the first disc portion having a first mating surface and joining a second set of additive layers of the second disc portion having a second mating surface and positioning the first mating surface of the first disc portion relative to the second mating surface of the second disc portion to form the implant disc.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A device comprising:
    a first disc portion being shaped and sized to correspond generally to a first intervertebral disc section including a pivot point positioned on a first surface opposite a second surface of the first disc portion and a first lattice structure with a negative Poisson's ratio; and
    a second disc portion being shaped and sized to correspond generally to a second intervertebral disc section including a pivot point receptacle positioned on a third surface opposite a fourth surface of the second disc portion and a second lattice structure with a negative Poisson's ratio;
    wherein the first disc portion is positioned relative to the second disc portion with the pivot point of the first disc portion within the pivot point receptacle of the second disc portion and the first surface of the first disc portion adjacent to the third surface of the second disc portion;
    wherein the first disc portion includes an endplate positioned adjacent and substantially parallel with the second surface of the first disc portion, and
    wherein the first disc portion and the second disc portion are configured to exhibit an auxetic behavior when subject to compression approximately perpendicular to a surface plane parallel to at least one of the first surface, the second surface, the third surface and the fourth surface.

2. The device of claim 1, wherein the endplate includes a threaded portion.

3. The device of claim 1, wherein the end plate includes a nano-porous material structured to allow biological material transfer.

4. The device of claim 1, wherein the second disc portion includes a second endplate approximate the fourth surface of the second disc portion.

5. The device of claim 1, comprising at least one vertical extension extending along a first outer surface of the first disc portion and a second outer surface of the second disc portion from a position approximate the second surface to a position approximate the fourth surface, the at least one vertical extension being orthogonal to the surface plane parallel to at least one of the first surface, the second surface, the third surface and the fourth surface.

6. The device of claim 5, wherein the at least one vertical extension further includes micro-porous channels with trabecular characteristics.

7. The device of claim 1, wherein the first disc portion includes an additive layer disc portion.

8. The device of claim 7, wherein the additive layer disc portion includes a plurality of layers joined to provide a sequential configuration of the first intervertebral disc section.

9. The device of claim 7, wherein the second disc portion includes a second additive layer disc portion having a plurality of layers joined to provide a sequential configuration of the second intervertebral disc section.

10. The device of claim 1 wherein the first surface comprises one or more protruding locating features; and
    the third surface comprises one or more locating pockets structured to engage the locating features.

11. The device of claim 1 wherein a layer of shock absorbing material is positioned between the first surface and the third surface.

12. A device comprising:
    a first disc portion of a intervertebral disc having a pivot point positioned relative to a first surface of the first disc portion; and
    a second disc portion of the intervertebral disc having a pivot point receptacle positioned relative to a second surface of the second disc portion,
    wherein the pivot point on the first surface of the first disc portion is positioned with respect to the pivot point receptacle on the second surface of the second disc portion to form the intervertebral disc,
    wherein the first disc portion includes an endplate positioned opposite the first surface of the first disc portion, and
    wherein the first disc portion and the second disc portion have a lattice structure configured to exhibit a negative Poisson's ratio when subject to compression perpendicular to a plane parallel to at least one of the first surface and the second surface.

13. The device of claim 12, wherein the endplate includes at least one feature selected from a group comprising antimicrobial characteristics, a nano-porous structure, outer threads, and a metamaterial structured to allow biological material transfer.

14. The device of claim 12, wherein the second disc portion includes a second endplate positioned opposite the second surface of the second disc portion.

15. The device of claim 12, wherein the first disc portion includes at least one vertical extension having microporous channels with trabecular characteristics.

16. The device of claim 15, wherein the first disc portion includes an additive layer disc structure and the second disc portion further includes a second additive layer disc structure.

17. The device of claim 16, wherein the additive layer disc structure includes a plurality of layers joined to provide a sequential configuration of the first disc portion of the intervertebral disc and the second additive layer disc structure further includes a plurality of layers joined to provide a sequential configuration of the second disc portion of the intervertebral disc.

18. A method comprising:
    analyzing an intervertebral space including a patient's intervertebral disc;
    creating a disc model in response to said analyzing;
    forming a first disc portion and a second disc portion with a plurality of additive layers in response to the disc model, each having a lattice structure configured to exhibit an auxetic behavior; and
    replacing the patient's intervertebral disc with an implant disc including the first disc portion and the second disc portion.

19. The method of claim 18, wherein said forming includes joining a set of additive layers of the first disc portion having a first mating surface and joining a second set of additive layers of the second disc portion having a second mating surface.

20. The method of claim 19, further including positioning the first mating surface of the first disc portion relative to the second mating surface of the second disc portion to firm the implant disc.

21. A method comprising:
creating a disc model for a patient based upon the patient's existing vertebral disc; and
forming a first disc portion and a second disc portion with a plurality of additive layers in response to the disc model, each having a lattice structure configured to exhibit an auxetic behavior.

* * * * *